United States Patent [19]

Whisson

[11] Patent Number: 5,498,245

[45] Date of Patent: Mar. 12, 1996

[54] ATTACHMENT FOR A PARENTERAL DEVICE

[75] Inventor: Maxwell E. Whisson, Nedlands, Australia

[73] Assignee: Eastland Technology Australia PTY LTD, Mount Lawley, Australia

[21] Appl. No.: 244,119

[22] PCT Filed: Nov. 20, 1992

[86] PCT No.: PCT/AU92/00622

§ 371 Date: May 19, 1994

§ 102(e) Date: May 19, 1994

[87] PCT Pub. No.: WO93/09824

PCT Pub. Date: May 27, 1993

[30]     Foreign Application Priority Data

Nov. 20, 1991 [AU] Australia ................. PK9593

[51] Int. Cl.⁶ ................................. A61M 5/32
[52] U.S. Cl. ................. 604/198; 604/192; 604/197; 604/263; 128/919
[58] Field of Search ................. 604/110, 181, 604/187, 192, 197, 198, 199, 240, 263; 128/919

[56]          References Cited

U.S. PATENT DOCUMENTS

| 4,941,883 | 7/1990 | Venturini | 604/186 |
| 4,994,042 | 2/1991 | Vadher | 604/165 |
| 5,000,167 | 3/1991 | Sunderland | 128/763 |
| 5,037,402 | 8/1991 | Bartman | 604/198 |
| 5,222,947 | 6/1993 | D'Amico | 604/198 |
| 5,263,942 | 11/1993 | Smedley et al. | 604/195 |
| 5,267,973 | 12/1993 | Haber et al. | 604/195 |
| 5,300,038 | 4/1994 | Haber et al. | 604/187 |
| 5,356,395 | 10/1899 | Chen | 604/263 |

FOREIGN PATENT DOCUMENTS

| 16234/88 | 4/1988 | Australia . |
| PCT/AU91/00297 | 7/1991 | WIPO . |

Primary Examiner—C. Fred Rosenbaum
Assistant Examiner—N. Kent Gring
Attorney, Agent, or Firm—Merchant, Gould, Smith, Edell, Welter & Schmidt

[57]          ABSTRACT

An attachment to a parenteral device (11) where the parenteral device (11) comprises a body (12) having a duct (15) which is convey a parenteral fluid, the attachment comprising a housing (20) adapted to be removably engageable with the body (12) and to be rigidly supported by the body when in engagement therewith, the housing (20) having a flow path (22, 23) which communicates with the duct (15) on engagement of the housing with the body; a hollow needle body (26) slidably supported within the housing (20) and comprising a hollow needle having a free end; the needle body (26) is slidably received within the housing (20) for movement between a first position at which the free end is received within the housing and a second position at which the free end extends from the housing, and the needle body is movable from the second position to the first position; a retaining means (27, 32, 33) provided to retain the needle body (26) in the first or second position; the needle having a first aperture (28) provided at or adjacent the free end, and a second aperture (29) provided in the needle body (26) spaced from the free end, the second aperture (29) bring in communication with the flow path (22, 23) when the needle body is in the second position.

21 Claims, 5 Drawing Sheets

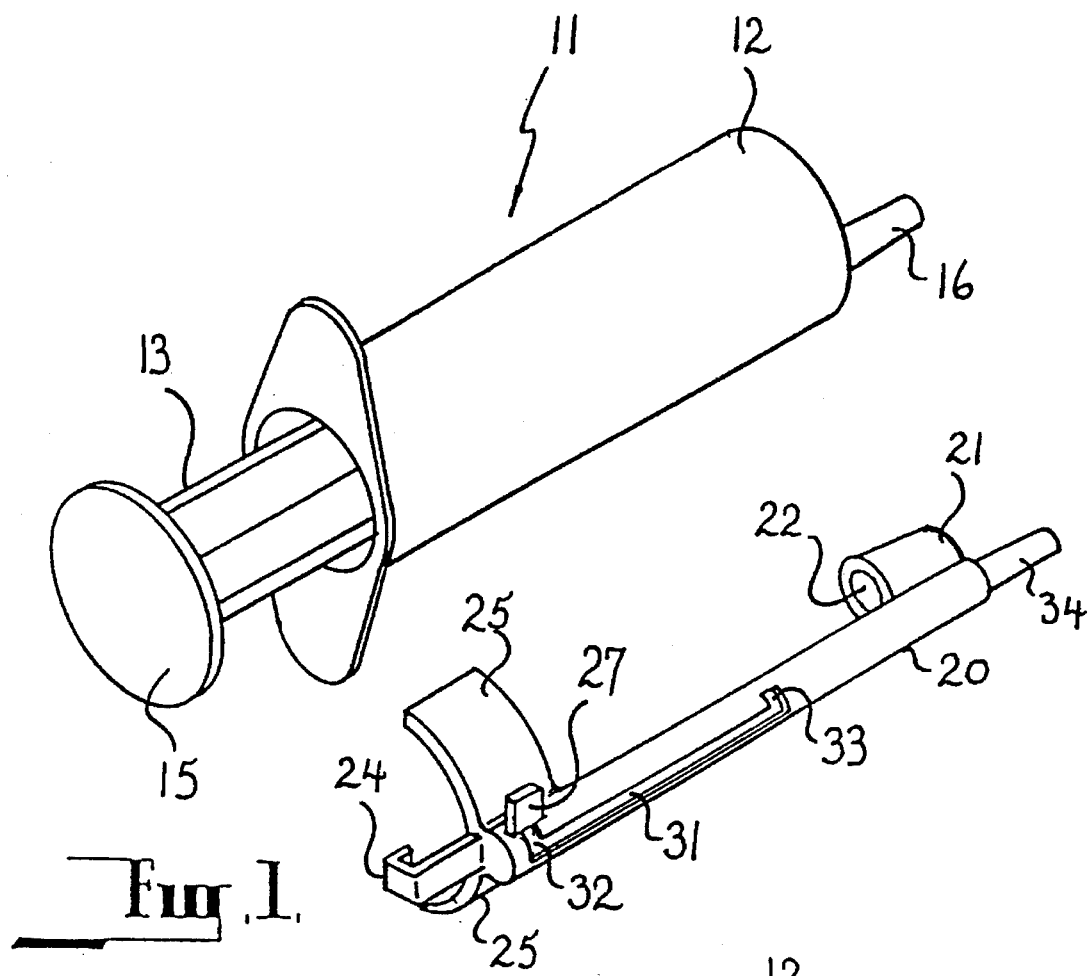
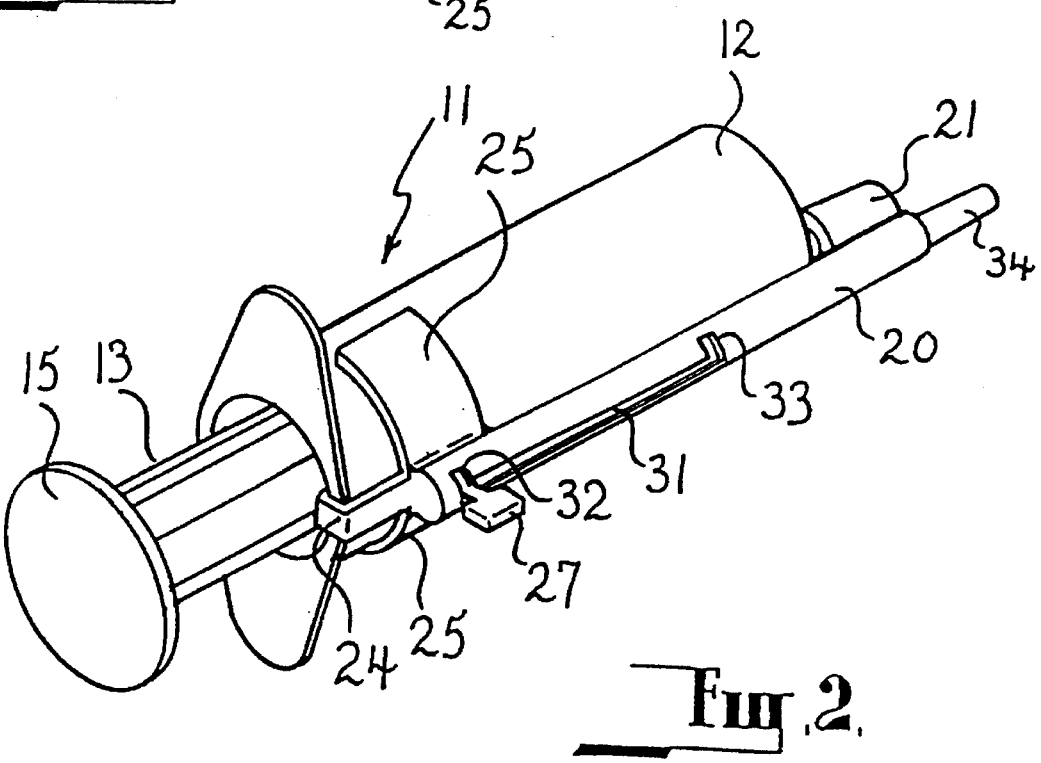

ATTACHMENT FOR A PARENTERAL DEVICE

Throughout this specification the term "parenteral device" shall be taken to include any device which can be used for the conveyance of parenteral fluids which are to be introduced into or drawn from the body and shall include within its scope a syringe, a cannula, hypodermic needle, intravenous infusion line and the like devices.

The parenteral device according to the invention relates to one in which the needle body which incorporates a needle is slidably supported in the body of the device to be movable between a first position at which the needle body and needle are fully accommodated within the body to be inaccessible and a second position at which the needle is caused to extend beyond the body whereby on the needle being moved to the second position it is in communication with a cheer or duct to or from which fluid can be transferred through the needle.

A difficulty which exists in relation to any form of parenteral device which incorporates a needle relates to the danger of inadvertent pricking of the user or another person during the assembly and utilisation of the device and its subsequent disposal.

Furthermore, while devices are available which provide for a retractable needle such devices are specialised.

It is an object of this invention to provide a parenteral device of the form described above where once the parenteral device has been used the needle can be withdrawn to be inaccessible. Furthermore it is an object of the invention to provide a device which can be used with existing parenteral devices.

Previously syringes have been proposed which incorporate retractable needles, however the interrelationship between the components of the syringe have resulted in a variety of complex arrangements. These forms of retractable syringe have been found to be of limited acceptability because of their complexity and consequent cost of manufacture.

Another arrangement is disclosed in EP 0479303 and comprises a retractable device which is to be attached to a specially modified syringe. The attachment accommodates a retractable needle. This device however requires that the needle be in an extended position prior to its use and on completion of the stroke of the plunger of the syringe the needle is irretrievably retracted into the body of the attachment. As a result the device does not avoid the possibility of an accidental "stick" injury or contamination prior to being used. This necessitates the utilisation of some form of protective cover for the needle prior to its use. In addition there are circumstances where it is not desirable to have the needle retract immediately on the plunger of the syringe completing its stroke in the syringe. In addition, less than careful operation of the device can lead to the inadvertent retraction of the needle which can itself be dangerous. Furthermore it is frequently necessary to remove the contaminated needle from the patient before the plunger has completed its stroke in the syringe so the need for retraction operated by the plunger is ineffective in such circumstances.

It is an object of the invention to provide an attachment which can be used with a conventional parenteral device and which enables a needle to be mounted to the parenteral device which can be extended and retracted in a controlled manner as required by the user.

In one form the invention resides in an attachment to a parenteral device where the parenteral device comprises a body having a duct which is to convey a parenteral fluid, said duct having a first opening at its outer end, said attachment comprising a housing adapted to be removably engagable with the body and to be rigidly supported by the body when in engagement therewith, a hollow needle body slidably supported within a passageway provided in the housing and comprising a hollow needle having a free end; said needle body being movable between a first position at which the free end is received within the housing and a second position at which the free end extends from the housing, and said needle body being movable from the second position to the first position; a retaining means provided to retain the needle body in the first or second position; said needle having a first aperture provided at or adjacent the free end, and a second aperture provided in the needle body spaced from the free end, said housing having a flow path extending between a second opening formed in the housing and the passageway, said second opening being adapted to be sealingly engaged with the first opening on engagement of the housing with the body; said second aperture being in communication with the flow path when the needle body is in the second position.

According to a preferred feature of the invention the parenteral device comprises a syringe.

According to a preferred feature of the invention the parenteral device comprises a cannula.

According to a further preferred feature of the invention the parenteral device comprises a cannula and the attachment parenteral device comprises an intravenous infusion line.

The invention will be more fully understood in the light of the following description of several specific embodiments. The description is made with reference to the accompanying drawings of which:

FIG. 1 is a schematic isometric view of a parenteral device and attachment of the embodiment prior to interengagement therebetween;

FIG. 2 is an isometric view of a parenteral device having the attachment of the embodiment applied thereto with the needle in the retracted position;

Figure 3:
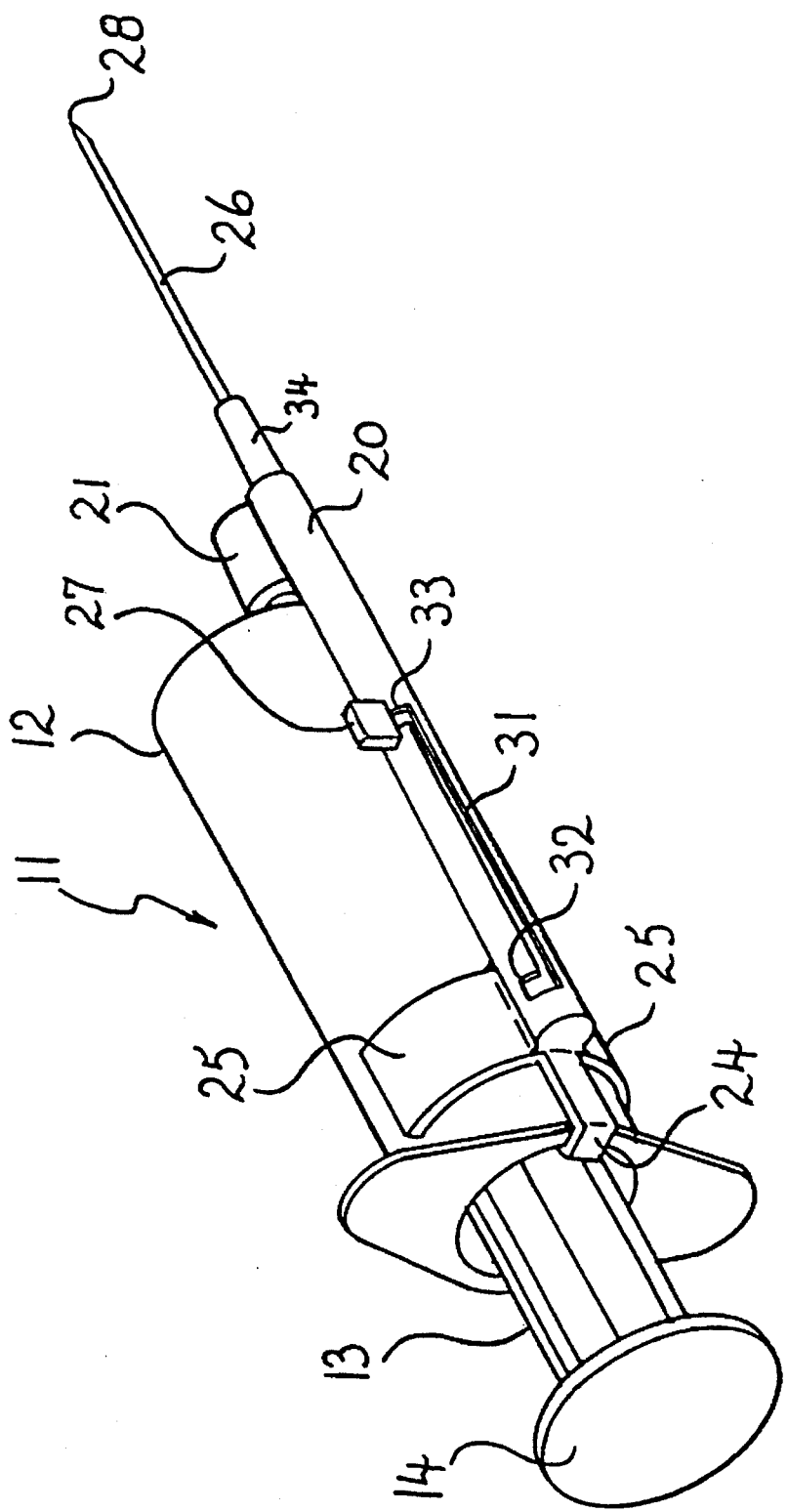
FIG. 3 is an isometric view of a parenteral device having an attachment according to the embodiment applied thereto with the needle in the extended position.

The first embodiment shown at FIG. 1 to relates to an attachment which is to be used with a parenteral device which takes the form of a conventional syringe. The syringe 11 comprises a cylindrical body 12 having a plunger slidably supported therein where the inner end of the plunger is formed with a piston which is sealingly engaged with the interior walls of the cylinder. The outer end of the plunger is provided with a handle 14. The closed wall of the syringe which is opposite the piston 14 of the plunger 13 is provided with an outlet duct 15 which is provided within a boss 16 on the end wall of the syringe. The syringe comprises a conventional form of syringe which would be used by applying a conventional needle to the tubular boss 16 by means of a "Luer" fitting or other form of fitting appropriate to support a needle from the syringe body or another tapered boss such as an ampoule piercing tip. If desired the boss may have a pointed tip to allow entry into soft bungs or ampoule caps.

The attachment according to the embodiment comprises a substantially tubular housing 20. The housing 20 is further provided with a lateral extension 21 which has a socket 22 having an axis which is substantially parallel with the housing 20 and is complementary to the configuration of the boss 16 provided on the syringe to be sealingly engagable therewith. The innermost end of the socket 22 opens into the interior of the housing 20 by means of a lateral duct 23.

The end of the housing 20 remote from the lateral extension 21 is formed with a bracket 24 in the form of a channel shaped flange which is spaced from the entry to the socket 22 by distance corresponding to the length of the body 12 of the syringe. The attachment of the embodiment is engaged with the body of the syringe by engagement of the boss 16 with the socket 22 of the housing and engagement of the bracket 24 over the edge provided at the opposite end of the syringe body. To stabilise the housing in position on the syringe body 12 a pair of lateral arms 25 are provided to each side of a housing intermediate its length which will partially surround the side wall of the body.

The lateral arms 25 partially encompass the body to be lockingly engaged therewith, once the attachment is located on the body 12 of the syringe. In addition the lateral arms take the form of plastic springs and are configured to snugly and clampingly engage the body of a variety of differing dimensioned syringes. In addition they may incorporate suction caps which will grip the body of the syringe.

The outer end of the housing is formed with a second tubular boss 34 which may be shaped to be engagable with a "Luer" fitting or any similar fitting, or may be pointed or bevelled to act as a bung piercing cannula.

The interior of the housing 20 accommodates a needle body 26 which includes a hollow needle. The needle body has a handle 27 at the end opposite the free end 28 of the needle. A first aperture is provided in the free end 28 while a second aperture 29 is provided at an intermediate position along the length of the needle. In addition a pair of seals 30 are provided in the interior of the housing to either side of the opening of the lateral duct 23 into the enclosed chamber. The seals 30 sealingly engage with the needle body to prevent the escape of fluid beyond the portion of the chamber located between the seals.

The socket 22, lateral duct 23 and portion of the interior of the housing 20 between the seals 30 provides the flow path between the tubular boss 16 of the syringe and the needle body.

Figure 4:
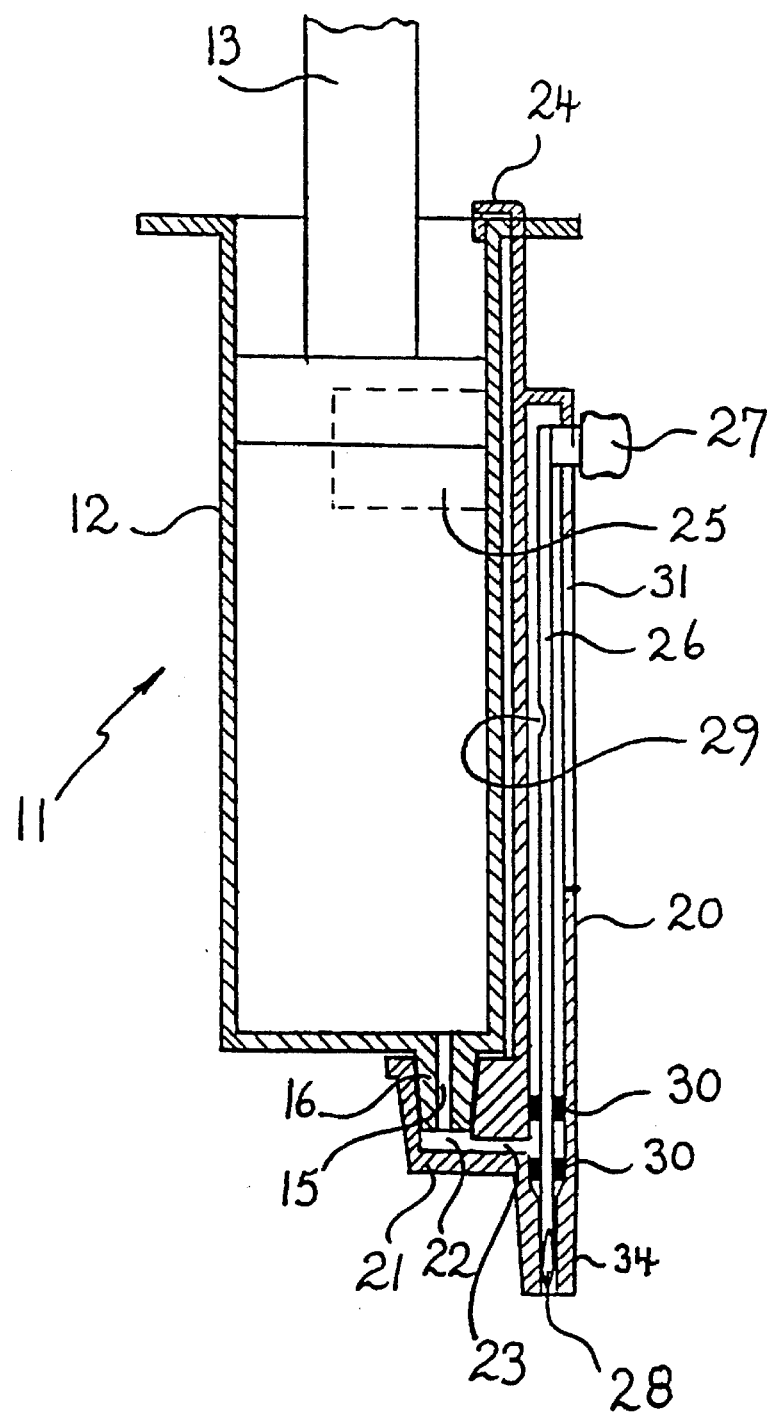
FIG. 4 is a sectional elevation of a parenteral device having the attachment according to the embodiment applied thereto showing the needle in the retracted position.
Figure 5:
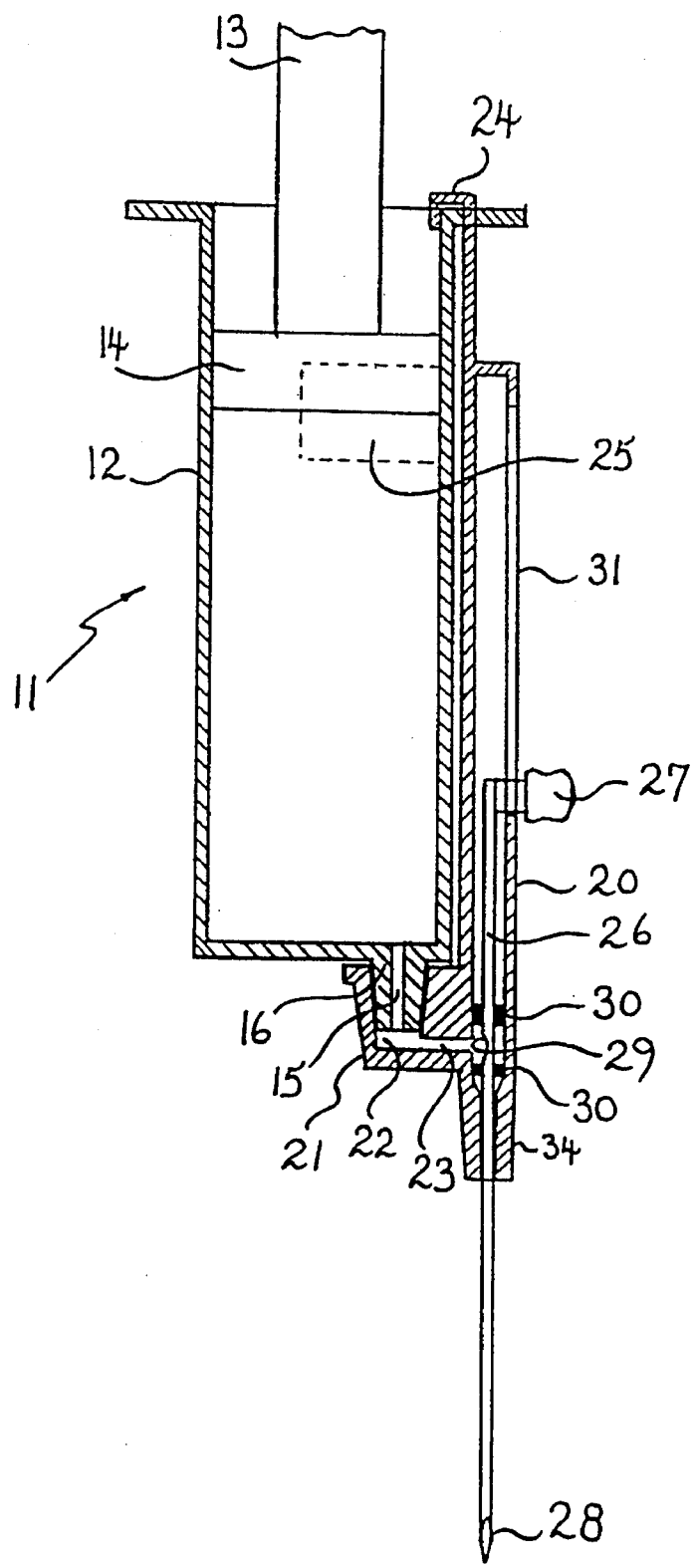
FIG. 5 is a sectional elevation of a parenteral device having an attachment according to the embodiment applied thereto with the needle in the extended position.

The side wall of the housing is formed with an axial slot 31 which facilitates axial movement of the handle 27 along the housing and thus axial movement of the needle body within the chamber between a retracted first position as shown at FIGS. 1, 2 and 4 at which the free end 28 is located within the housing and an extended second position as shown at FIGS. 3 and 5 at which the free end extends beyond the housing and the second aperture 29 is located in the space between the seals 30. When the needle is in its second position the interior of the needle body is in open communication with the interior of the syringe through the flow path to facilitate the transfer of parenteral fluid. The ends of the slot 31 in the wall of the housing 20 is formed with a part circumferential extension 32 and 33 which enables the needle body to be locked in the first and second position by engagement of the handle in the respective extension.

In use a conventional syringe has the attachment applied thereto by engaging the boss of the syringe into the socket 22 of the attachment and the flange 24 provided at the other end of the housing with the edge of the body of the syringe remote from the boss. Once the attachment has been engaged with the syringe the needle body is moved to its extended position such that the second aperture therein is in open communication with the interior of the syringe and interior of the needle. This communication is via the duct 15 which is provided in the boss and the flow path of the attachment which comprises, the socket 22 the lateral duct 23 and the interior of the housing between the seals 30. This communication enables the transfer of parenteral fluid to or from the syringe as desired. When it is required to dispose of the syringe the needle body can then be retracted to within the housing by movement of the handle 27 towards the end of the axial slot 31 remote from the socket 22 and indexing the handle into the part circumferential exterior 32 provided in the slot 31. The entry of the extension 32 may be of reduced width so as to render passage of the base of the handle 27 into the slot 32 difficult if not irreversible. If desired the handle may be capable of being separated from the needle body when moved into the extension. The attachment can then be removed from the syringe and discarded.

If desired when the needle body when at its retracted position in the housing the needle may be positioned such that the free end is inward of the passageway formed in the second boss 34 of the attachment and from the outermost seal 30 between the wall of the housing and the needle body. In such an instance the interior of the housing accommodates a further seal at a position corresponding to the position of the second aperture 29 when the needle body is retracted to sealingly close the second aperture. As a result the attachment can be used for drawing into the syringe a parenteral agent. Such action can be effected by utilization of the second boss 34 or a needle which is applied to the second boss in a conventional manner. In such an instance the second boss can be configured to have a pointed tip to allow entry into a soft bung or ampoule cap.

If desired an interengagement means may be provided between the interior of the housing 20 and the needle body to facilitate locking engagement therebetween on the needle body being moved from the extended position to the retracted position to prevent the reuse of the needle. Furthermore means may be provided such that on completion of the use of the attachment the movement of the needle body to the retracted position effects at least partial destruction of at least one of the seals 30 provided within the chamber of the housing 20 which prevents effective reutilization of the attachment. In such an instance the needle body is capable of occupying an intermediate position in the housing at which position the needle body is fully received within the housing, the needle body is located in the intermediate position prior to its use.

The embodiment provides a means whereby a conventional syringe can be used in a conventional manner but where the dangers of which are inherent in the mounting and use of a conventional pointed needle to that syringe are avoided. The embodiment also provides a means whereby a syringe with an unconventional or non-standard boss 16 may be adapted to take a conventional needle and at the same time provide a retractable needle.

As an alternative to the seals the needle body may be formed with an annular enlargement in the region of the second aperture 6r to each side of the second aperture which will sealingly engage the interior wall of the housing to each side of the lateral duct 23. This arrangement is most easily achieved by constructing seals 30 as an elastic enlargement in the diameter of the needle body 26 around aperture 29.

Another construction comprises the needle body incorporating an enlarged portion mounted to the other end of the needle. The enlarged portion accommodates the second aperture and is dimensioned to be sealingly received within the housing.

Figure 6:
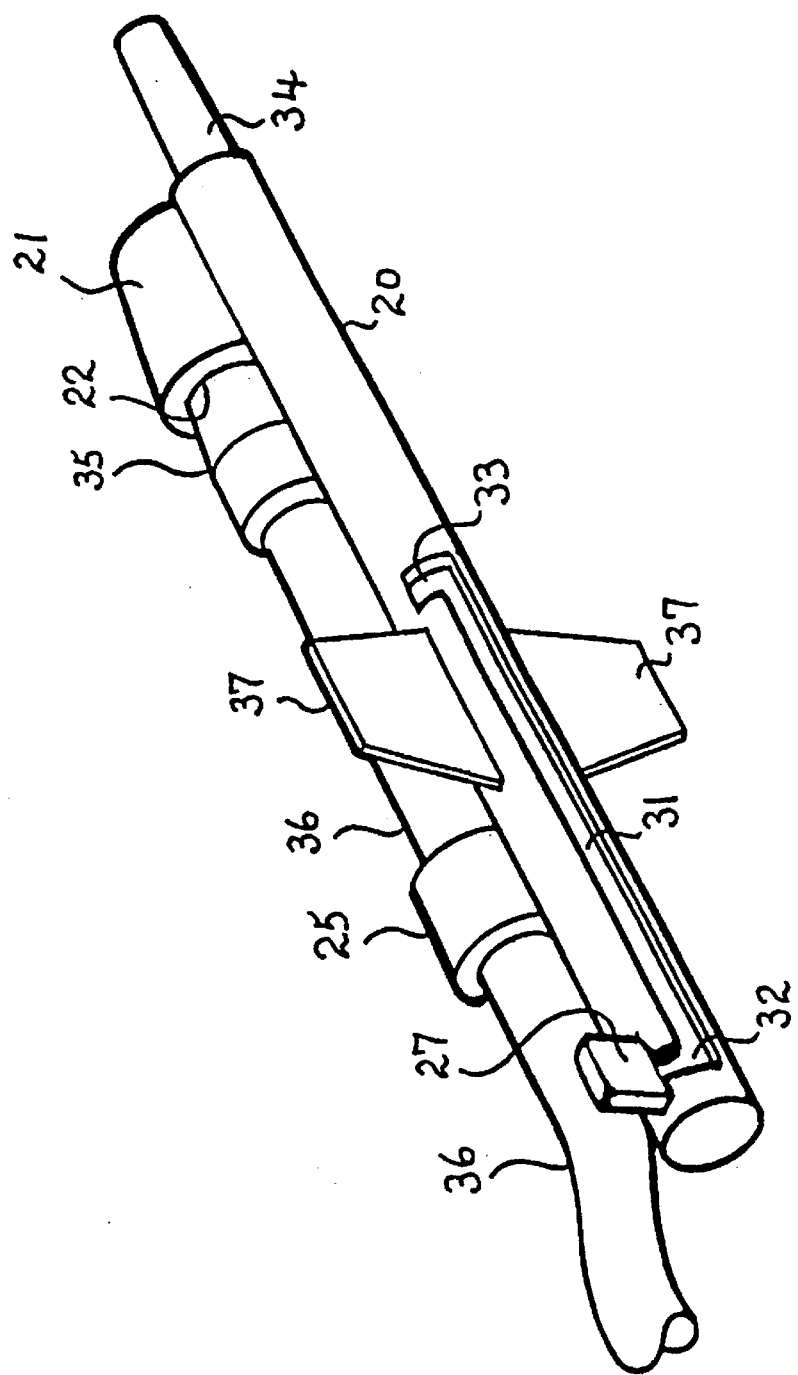
FIG. 6 is an isometric view of a second embodiment which is a cannula used with an intravenous infusion line.

The second embodiment shown at FIG. 6 is of a similar form to the first embodiment and the same reference numerals have been used for identical components. The lateral arms 25 are dimensioned to resiliently receive and support an intravenous line while the cannula fitting 35 is sealingly received in the socket 22. Support wings 37 are mounted to each side of the housing to provide for lateral support for the attachment when in position on the patients body.

It should be appreciated that the present invention need not be limited to application for use in respect of a syringe but may have application to any form of parenteral device including cannulas and the like.

The claims defining the invention are as follows:

1. An attachment to a parenteral device where the parenteral device comprises a body having a duct which is to convey a parenteral fluid, said duct having an opening at an outer end; said attachment comprising a housing adapted to be removably engagable with the body and when in engagement with the body to be rigidly supported thereby; a passageway provided within the housing; a needle body comprising a hollow needle having a free end; said needle body being movable between a first position at which the free end is received within the housing and a second position at which the free end extends from the housing; said needle body being movable from the second position to the first position; a retaining means provided to retain the needle body in the first or second position; said needle having a first aperture provided at or adjacent the free end, and a second aperture provided in the needle body spaced form the free end, said housing having a flow path extending between a second opening formed in the housing having a flow path extending between a second opening formed in the housing and the passage way; said second aperture adapted to be in communication with the flow path when the needle body is in the second position; said second opening being adapted to be sealingly engaged with the first opening on the body of the parenteral device when the housing is supported by the body.

2. An attachment as claimed at claim 1 wherein the duct of the parenteral device is at least partially accommodated in a tubular boss which extends from the body and the first opening is located at the outer end of the boss, wherein the second opening of the engagement is provided in a socket which is shaped to be sealingly engaged with the boss.

3. An attachment as claimed at claim 2 wherein the housing is formed with a laterally directed bracket which is engagable with the body at a position spaced from the socket, said socket and bracket being offset laterally on the housing and being adapted to engage the body in opposed relation to each other.

4. An attachment as claimed at claim 3 wherein the housing is formed with at least one lateral arm which extends laterally from the housing, said at least one lateral arm being configured to at least partially extend around the body and clampingly engage the body.

5. An attachment as claimed at claim 2 wherein the needle body is formed with a handle which extends laterally from the housing through an axial slot in the housing whereby slidable movement of the handle in the slot causes the slidable movement of the needle body.

6. An attachment as claimed at claim 5 wherein the retaining means comprises a lateral extension of said slot at two spaced locations along the length of the slot corresponding to the respective locations of the handle when the needle body is at its first and second position, said needle body being capable of rotation within the housing to enable the handle to be located in the respective lateral extension when the needle body is at its first and second position.

7. An attachment as claimed at claim 6 wherein the lateral extensions have an entry of reduced width.

8. An attachment as claimed at claim 7 wherein the housing is substantially tubular to provide the passageway and a seal is provided within the passageway to each side of the flow path, said seals sealingly engaging the needle body.

9. An attachment as claimed at claim 2 wherein the housing is formed with at least one lateral arm which extends laterally from the housing, said at least one lateral arm being configured to at least partially extend around the body and clampingly engage the body.

10. An attachment as claimed at claim 9 wherein the needle body is formed with a handle which extends laterally from the housing through an axial slot in the housing whereby slidable movement of the handle in the slot causes slidable movement of the needle body.

11. An attachment as claimed at claim 2 wherein the housing is substantially tubular to provide the passageway and a seal is provided within the passageway to each side of the flow path, said seal sealingly engaging the needle body.

12. An attachment as claimed at claim 11 wherein means is provided on the needle body to render said seal inactive on said needle body being moved to said second position from said first position.

13. An attachment as claimed at claim 12 wherein lock means is provided between he housing and the needle body, to lock the needle body in position in the housing on the needle body being moved from said first position to said second position.

14. An attachment as claimed at claim 11 wherein lock means is provided between the housing and the needle body, to lock the needle body in position in the housing on the needle body being moved from said first position to said second position.

15. An attachment as claimed at claim 2 wherein a locking means is provided between the housing and the needle body, said locking means being adapted to hold the needle body in position in the housing when the needle body has been moved from said first position to said second position.

16. An attachment as claimed at claim 15 wherein said passageway has a length such that said needle body occupies an intermediate position between said first position and said second position at which said intermediate position the free end is accommodated within the housing and said retaining means is able to retain the needle body in the intermediate position.

17. An attachment as claimed at claim 1 wherein the parenteral device comprises a syringe.

18. An attachment to a parenteral device where the parenteral device comprises a body having a duct which is to convey a parenteral fluid, said duct having an opening at an outer end; the duct of the parenteral device is at least partially accommodated in a tubular boss which extends from the body and the first opening is located at the outer end of the boss, the housing is substantially tubular to provide the passageway and a seal is provided within the passageway to each side of the flow path, said seal sealingly engaging the needle body; said attachment comprising a housing adapted to be removably engagable with the body and when in engagement with the body to be rigidly supported thereby; a passageway provided within the housing; a needle body comprising a hollow needle having a free end; said needle body being movable between a first position at which the free end is received within the housing and a second position at which the free end extends from the housing; said needle body being movable from the second position to the first position; a retaining means provided to retain the needle body in a position; said needle having a first aperture provided at or adjacent the free end, and a second aperture provided in the needle body spaced from the free end, said housing having a flow path extending between a second opening formed in the housing and the passage way; said second aperture adapted to be in communication with the flow path when the needle body is in the second position; said second opening being adapted to be sealingly engaged with the first opening on the body of the parenteral device when the housing is supported by the body.

19. The attachment as claimed in claim 18 wherein means is provided on the needle body to render said seal inactive on said needle body being moved to said second position from said first position.

20. An attachment to a parenteral device where the parenteral device comprises a body having a duct which is to convey a parenteral fluid, said duct having an opening at an outer end; said attachment comprising a housing adapted to be removably engagable with the body and when in engagement with the body to be rigidly supported thereby; a passageway provided the within housing; a needle body comprising a hollow needle having a free end; said needle body being movable between a first position at which the free is received within the housing and a second position at which the free end extends from the housing; said housing is substantially tubular to provide the passageway and a seal is provided within the passageway to each side of the flow path, said seals sealingly engaging the needle body said needle body being movable from the second position to the first position; said the needle body is formed with a handle which extends laterally from the housing through an axial slot in the housing whereby slidable movement of the handle in the slot causes the slidable movement of the needle body a retaining means provided to retain the needle body in the first or second position; said wherein the retaining means comprises a lateral extension of said slot at two spaced locations along the length of the slot corresponding to the respective locations of the handle when the needle body is at its first and second position, said needle body being capable of rotation within the housing to enable the handle to be located in the respective lateral extension when the needle body is at its first and second position; said lateral extensions have any entry of reduced width said needle having a first aperture provided at or adjacent the free end, and a second aperture provided in the needle body spaced form the free end, said housing having a flow path extending between a second opening formed in the housing having a flow path extending between a second opening formed in the housing and the passage way; said second aperture adapted to be in communication with the flow path when the needle body is in the second position; said second opening being adapted to be sealingly engaged with the first opening on the body of the parenteral device when the housing is supported by the body.

21. An attachment as claimed at claim 20 wherein a lock means to lock the needle body in position in the housing is provided between the housing and the needle body.

* * * * *